United States Patent [19]

Penenberg et al.

[11] Patent Number: 4,808,185
[45] Date of Patent: Feb. 28, 1989

[54] TIBIAL PROSTHESIS, TEMPLATE AND REAMER

[76] Inventors: Brad L. Penenberg, 19 Charles St., Braintree, Mass. 02184; Murali Jasty, 7 Arden Rd., Wellesley, Mass. 02181; Hugh P. Chandler, Lewis Wharf 438, Boston, Mass. 02110

[21] Appl. No.: 827,148

[22] Filed: Feb. 7, 1986

[51] Int. Cl.$^4$ .......................... A61F 2/38; A61F 2/30
[52] U.S. Cl. ......................................... 623/20; 623/18
[58] Field of Search .................. 623/20, 21, 22, 23, 623/18

[56] References Cited

U.S. PATENT DOCUMENTS

| | | | |
|---|---|---|---|
| 4,224,696 | 9/1980 | Murray et al. | 623/20 |
| 4,257,129 | 3/1981 | Volz | 623/20 |
| 4,479,271 | 10/1984 | Bolesky et al. | 623/18 |

FOREIGN PATENT DOCUMENTS

| | | | |
|---|---|---|---|
| 0121002 | 10/1984 | European Pat. Off. | 623/22 |
| 0135319 | 3/1985 | European Pat. Off. | 623/20 |
| 2349357 | 4/1975 | Fed. Rep. of Germany | 623/22 |
| 2845231 | 5/1979 | Fed. Rep. of Germany | 623/22 |
| 2465470 | 4/1981 | France | 623/18 |
| 2478462 | 9/1981 | France | 623/18 |
| 0483980 | 9/1977 | U.S.S.R. | 623/23 |
| 1333412 | 10/1973 | United Kingdom | 623/20 |
| 2004465 | 4/1979 | United Kingdom | 623/20 |
| 2061730 | 5/1981 | United Kingdom | 623/20 |

Primary Examiner—V. Millin
Assistant Examiner—David J. Isabella
Attorney, Agent, or Firm—Sherman and Shalloway

[57] ABSTRACT

Disclosed herein are an improved tibial prosthesis and a template and reamer which are utilized in installing the prosthesis on the proximal end of a surgically prepared tibia. The prosthesis comprises a tibial component including a tray attached to the proximal tibia and an insert attached to the tray and provided to present an articulating surface for bearing engagement with the distal end of the femur or alternatively with a femoral component which has been surgically attached to the distal end of the femur. The tray includes an exterior surface including a plurality of domical contours which interengage with corresponding surfaces formed in the proximal tibia by the surgeon. The tray is preferably attached to the proximal tibia through the use of screw fasteners extending through openings formed in the domical contours. The template is utilized by the surgeon in measuring the exact location and size of the contours which are to be surgically formed in the proximal tibia. The reamer is specifically designed to enable its use during the surgical procedure to surgically create the contours which are formed in the proximal tibia.

10 Claims, 4 Drawing Sheets

TIBIAL PROSTHESIS, TEMPLATE AND REAMER

BACKGROUND OF THE INVENTION

The present invention relates to an improved tibial prosthesis, template and reamer. The bearing surfaces of the knee joint are vulnerable to stress and arthritic and other disease-induced deterioration. Prosthetic correction is indicated when the knee joint is so damaged that other less drastic techniques have little or no prospect of success. In earlier years, hinge-type prostheses were most frequently employed in such cases to restore the joint to some degree of normalcy. This was not entirely satisfactory due to the complexity of the knee joint movement, the desirability of minimal bone removal, the need for preserving potentially functional cruciate and collateral ligaments, and the limitations of hinge-type prostheses in handling various knee loads and forces without being damaged. Hinge-type prostheses are generally limited today to cases with severe soft tissue damage. Later and present knee prostheses have separate femoral and tibial components attached to the respective femoral and tibial condyles so as to provide a prosthesis more in harmony with the actual workings of the knee joint. Separate components allow use of the existing cruciate and collateral ligaments and permit the prosthesis to handle radial and twisting forces on the knee without breaking.

Although the prior art as embodied in separate tibial and femoral components has become more sophisticated as of late, to this time, tibial prosthetic components do not ideally replace the bone tissue since their shapes and means of attachment do not optimize the uniform spreading of forces which are placed on the tibia nor do they adequately oppose lateral motions which are inherently placed upon tibial components during normal joint movements. Thus, in the prior art, tibial components often loosen and must be reattached or replaced with such operations often requiring removal of additional bone tissues.

In a further aspect, many tibial components known at this time are attached to the proximal tibia through the use of cementing techniques. This may cause problems in the joint since these cementing techniques usually result in elevated temperatures during the curing of the cement, which elevated temperatures tend to damage body tissues. Thus, a need has developed for a tibial prosthesis which may be installed without the use of cement but which may consistently achieve firm initial fixation and thence may receive bony ingrowth for firm permanent fixation.

The tibial component of a knee prosthesis is generally cemented to the tibial condyle rather than screwed thereto because a satisfactory environment for uncemented devices has not been taught by prior art. Earlier tibial components such as that which is disclosed in U.S. Pat. No. 3,728,742 to Averill had serrations and pins on the underside which were anchored in the proximal tibial surface by a suitable cement after surgical preparation. The problems with cemented prosthesis have been discussed hereinabove and components such as those disclosed by Averill have been known to be vulnerable to loosening from typical knee forces which are placed on the prosthesis.

In order to avoid the problems of Averill, the configuration of the tibial component further evolved to a point where a vertical element extending downwardly from the undersurface of the tibial component and into the tibia has been used to counteract instability problems. U.S. Pat. No. 4,205,400 to Shen, et al. discloses a tibial prosthesis having a base plate formed with a depending connecting stem which is designed to extend distally into the proximal tibial surface into a cavity excavated therein by the surgeon. This device is believed to be deficient in that it requires a large amount of bone removal and still requires the use of cement which has the problems as set forth hereinabove.

Additionally, the following prior art is known to applicants:

U.S. Pat. No. Re. 29,757 to Helfet discloses prosthetic joint components including double curved surfaces as well as an elongated post for fixation purposes. The teachings of Helfet differ from the teachings of the present invention mainly because the present invention does not require an elongated fixation spike and further because the present invention utilizes fixation means which may comprise screws extending through the curved surfaces thereof.

U.S. Pat. Nos. 4,224,696 and 4,224,697 both to Murray, et al., disclose a prosthetic knee having femoral and tibia components both of which are made of a biologically inert high strength metal such as chromium-cobalt-molybdenum. The meniscal plate is a one-piece unit of ultra-high molecular weight polyethylene and fixed between the femoral and tibial components. The underside of the tibial component include a substantially curved surface but also requires an elongated anchoring spike. Of course, this anchoring spike renders the tibial prosthesis of Murray, et al. vastly different from the teachings of the present invention and Murray, et al. also fail to disclose the type of fixation utilized in the present invention.

SUMMARY OF THE INVENTION

The present invention overcomes the deficiencies found in prior art tibial prostheses such as those discussed above and provides an improved tibial prosthesis which optimizes prosthesis design and insertion and retention techniques. The inventive tibial prosthesis optimizes the design by providing a structure which optimally spreads forces in more than one direction into the tibia so as to reduce the effects of shock forces and lateral joint movements which may occur in normal walking motions. Furthermore, the inventive prosthesis increases the surface area of engagement between the prosthesis and the bone surface so as to maximize the area of the engaging surfaces and thereby maximize the area of fixation therebetween. By increasing the surface area through the use of a plurality of domical surfaces, lateral motion of the prosthesis with respect to the bone is substantially avoided. Furthermore, the present invention by eliminating elongated fixation posts reduces the amount of bone material which must be removed from the bone during the installation of the prosthesis during surgery.

The present invention includes the following aspects:

(a) The improved tibial prosthesis forming a part of the present invention is made of two general parts. The first part comprises a tray portion preferably made of a metallic material. The tray portion includes in the preferred embodiment a double domical contour which is designed to face the cut surface of the proximal tibia. The domes which define the domical contour provide anatomical and physiological interfaces with the bone of the proximal tibia as it has been prepared by the surgeon and is distinct from the prior art as using large convex undersurfaces to fixate the prosthesis to the proximal tibia without the additional use of elongated peg-type fastening means. By providing the domical contours, the tray portion maximizes the surface area of interengagement between the tray portion and the bone surfaces of the proximal tibia over the area which would be in interengagement were the contour of the tray portion to be made completely flat. This increased surface area enhances bony ingrowth fixation and eliminates the need for bone cement where bony ingrowth fixation is indicated in particular cases.

(b) Each of the domes which form the domical contour has, in the preferred embodiment, a plurality of holes therein through which fastening devices are extended so as to fasten the tray portion to the proximal tibia. In the preferred embodiment, these fastening devices consist of headed screws, however, if desired, other fixation devices such as nails may be utilized. In order to enhance the fixation of the tray portion to the bone surfaces, the domical contours may be provided with metallic or non-metallic mesh bony ingrowth materials specifically designed to interact with the bone tissue of the tibia so that the bone tissue grows therein to thereby permanently fixate the tray portion to the bone. These factors combined with the fact that the convexities of the undersurface of the tray portion are analogous to the normal contours of the sub-chondral bone optimizes the firm fixation of the tray portion to the bone. In a further aspect, the convexities reproduce the normal distribution of stress within the cancellous and cortical bone of the proximal tibia. If desired, the above-described metal bony fixation material may instead consist of a porous bony ingrowth fixation layer.

(c) The other part of the tibia prosthesis consists of an articular insert preferably made of a low friction plastic material. The insert is designed to be attached to the back side of the tray portion in any suitable manner such as for example, through a snap fit connection, dove-tail interface or through the use of fastening devices such as screws. In another aspect, in practice, fastening means to fasten the tray portion and articular insert portion together are not necessary since the various knee ligaments and tendons, if intact, will hold the portions together. The plastic insert on its face which faces away from the tibia includes a bearing surface designed to engage the distal end of the femur or, alternatively, distal surfaces of a distal femur prosthesis.

(d) In a further aspect of the present invention, in order to properly install the tibial prosthesis on the tibia, the proximal tibia must be properly and accurately prepared for the installation of the prosthesis. For this purpose, the present invention further includes a template which is designed to enable the surgeon to properly locate the areas on the proximal tibia where recesses are to be formed so as to enable the proximal tibia to snugly receive the domical contours. Thus, the present invetion includes such a template which includes a plurality of holes therethrough corresponding to the number of domes which are to be included in the prosthesis and further includes a peripheral shape corresponding closely to the periphery of the bone surface which has been prepared by the surgeon. Thus, the template may be placed over the bone surface and a reamer device may easily be guided through the template holes and thereby used to ream the domical recesses in the proximal tibia.

(e) In order to ream the domical recesses in the proximal tibia, a special reaming device must be utilized since the reaming device will be utilized through a body incision during the course of surgery. Thus, the present invention further contemplates a special reamer having a drive shaft preferably disposed at an angle to the axis of rotation of the reaming head. In the preferred embodiment, this angle should be from 45° to 90°, however, other angles may be contemplated by those skilled in the art so long as those angles enable the reamer to be utilized through an incision in the knee.

In a further aspect of the present invention, the domical contours of the tray portion may take on different types of curvature. Thus, for example, the individual domes may be part-spherical or elliptical in nature. It is important to note that the present invention solely resides with the creation of domical contours of curved configuration since applicants believe that such curved configurations optimize the distribution of stresses and forces which are created through the use of a knee in normal movements thereof. The inventors believe that other types of surfaces such as for example conical surfaces, do not properly distribute the forces and stresses which are imposed upon a knee joint during normal motions thereof and thus such conical surfaces are inferior to the teachings of the present invention. In the situation where the domes are made of spherical surfaces, it has been found that, optimally, each dome comprises less than a hemisphere. This is because completely hemispherical domes would require the removal of too much bone tissue from the proximal tibia and would thus cause a negative impact thereon. It has been found that spherical surfaces describing less than a hemisphere increase the surface area of contact between the proximal tibia and the domical contours sufficiently so as to render them quite reliable.

Accordingly, it is a first object of the present invention to provide a new and improved tibial prosthesis for an articular knee joint prosthesis.

It is a further object of the present invention to provide such a prosthesis which increases the surface area of engagement between the prosthesis and the proximal tibia.

It is a still further object of the present invention to provide such a prosthesis which spreads forces and stresses which are placed on a knee joint during normal movements thereof so as to reduce the possibilities of lateral motion of the prosthesis with respect to the tibia.

It is a still further object of the present invention to provide such a prosthesis which increases the surface area of interengagement while reducing the amount of material which must be removed from the tibia.

It is a still further object of the present invention to provide such an improved tibial prosthesis which increases the surface area of interengagement to a sufficient extent so as to avoid the necessity of cementing the prosthesis to the proximal tibia and so as to facilitate fixation through the use of bolt or screw fasteners.

It is a yet further object of the present invention to provide a tibial prosthesis which substantially duplicates the anatomical configuration of the sub-chondral plates in the medial and lateral compartments of a healthy knee joint.

It is a still further object of the present invention to provide a template and reamer device which are specifically designed to enable the accurate preparation of the proximal tibia for the installation of the improved tibial prosthesis of the present invention.

These and other objects, aspects and features of the present invention will be better understood in the following detailed description of the preferred embodiments when read in conjunction with the appended drawing figures.

SPECIFIC DESCRIPTION OF THE PREFERRED EMBODIMENTS

Figure 1:
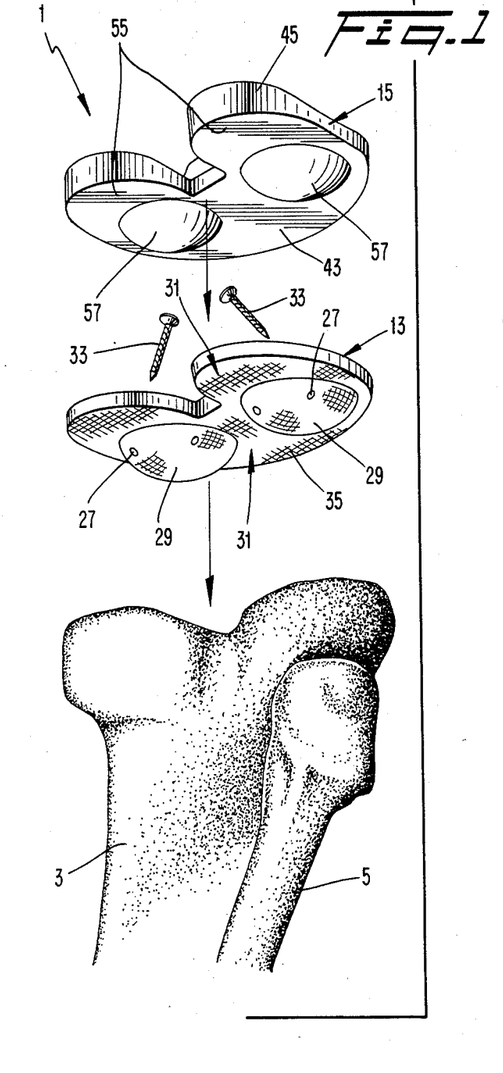
FIG. 1 shows an exploded perspective view, from below, of a first embodiment of the prsent invention.
Figure 2:
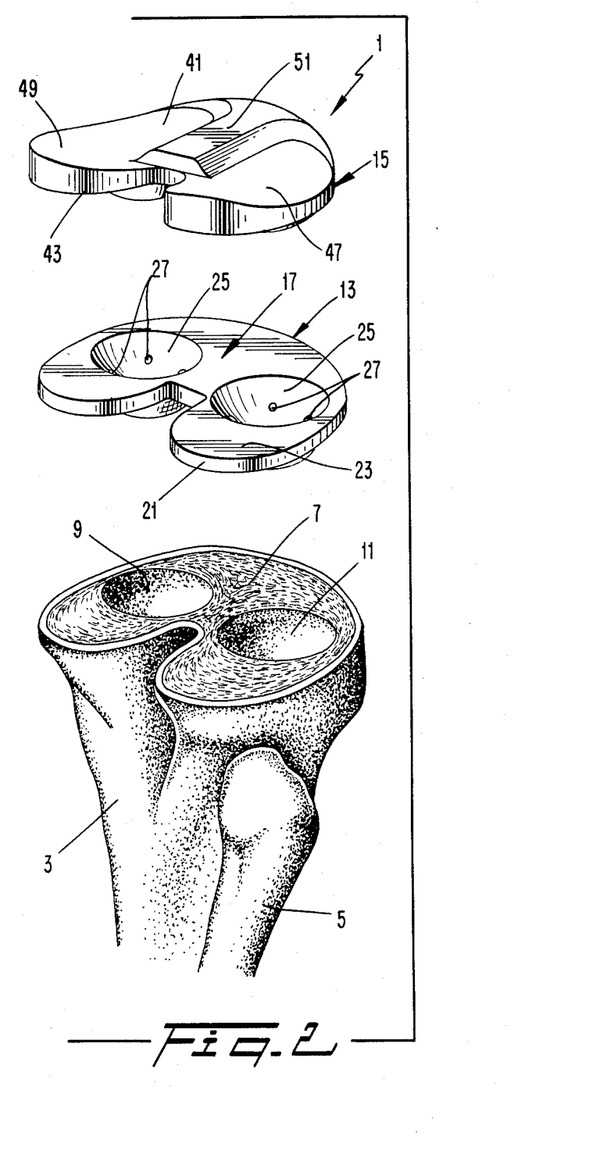
FIG. 2 shows a further exploded perspective view, from above, of the embodiment of FIG. 1.

Reference is first made to FIGS. 1, 2, 3 and 4 wherein a first embodiment of the present invention is shown in detail. Reference numeral 1 refers generally to the tibial prosthesis comprising the major aspect of the present invention. As shown in FIGS. 1 and 2, the tibia 3 is adjacent the fibula 5 which is the non-weight bearing lower leg bone. As is well known and not shown herein, the tibia has a plateau portion made up of a lateral plateau and a medial plateau with each plateau having a pronounced indentation, which indentations are termed the lateral sub-chondral plate and the medial sub-chondral plate. Stress transfer from a load-bearing femur to the proximal tibia is by way of the sub-chondral plates named above. Thus, the tibial bone structure consisting of cancellous and cortical tissue in the areas of the sub-chondral plates is consequently denser and stronger than bone tissue in other areas of the tibia.

As may be seen with particular reference to FIG. 2, in order to prepare for installation of the prosthesis of the present invention, the proximal tibia has been prepared by the surgeon to have a flat surface 7 thereon into which are reamed a plurality of domical recesses, in this example, two in number and designated by the reference numerals 9 and 11. The number of domical recesses which are prepared in the proximal tibia corresponds to the number of domical contours which are included in the tray portion of the inventive prosthesis.

The inventive prosthesis 1 includes a tray portion generally designated by the reference numeral 13 and an articular insert portion generally designated by the reference numeral 15.

The tray portion 13 includes an upper surface 17, a lower surface 19 and a peripheral surface 21. The upper surface 17 consists of a flat portion 23 and a plurality of domical recesses each designated by the reference numeral 25. As seen in FIGS. 1 and 2, a plurality of holes 27 extend through the tray portion 13 which holes 27 originate in the recesses 25.

The tray periphery 21 is of a substantially C-shaped configuration which is specifically designed to match the outer periphery of the proximal tibia as it has been prepared by the surgeon for implantation of the prosthesis 1. This may be seen from comparison of the periphery 21 and the periphery of the proximal tibia as best seen in FIG. 2. With reference to FIG. 1, the underside surface 19 of the tray portion 13 includes a contoured surface comprising, in this example, a pair of domical contours 29 through which the holes 27 extend. As stated above, the domical contours 29 are characterized by having curved surfaces which may be formed through rotation of a curved line about its axis of rotation. In the embodiment shown in FIGS. 1-4, the domical contours 29 consits of part spherical surfaces. As will be described in greater detail hereinafter, domical contours comprising other types of curved surfaces may also be contemplated under the purview of the present invention.

With further reference to FIG. 1, it is seen that in surrounding relation to the domical contours 29, the undersurface 19 of the tray portion 13 includes flat surfaces 31 which extend to the periphery 21. The flat surfaces 31 are designed to bearingly engage the flat surfaces 7 of the proximal tibia as best seen in FIG. 2 while the domical contours 29 are specifically sized and designed so as to interengage in the domical recesses 9 and 11 which have been prepared in the poximal tibia. If desired, the domical contours 29 may cover as much as 75% of the surface area of the tray undersurface 19 or more if desired. In the preferred embodiment, screws designated by the reference numeral 33 in FIG. 1 may be inserted through the holes 27 within the recesses 25 to the top surface 17 and thence screwed into the proximal tibia preferably within the domical recesses 9 and 11 which have been formed therein to thereby fixate the tray portion 13 to the proximal tibia. Of course, the fasteners may extend through any portion of the tray portion and thence into the proximal tibia. Regardless of where the fasteners are located, the domical contours will just as effectively uniformly spread forces placed on the prosthesis throughout the tibia. For example, the fasteners could extend through the tray portion without intersecting with any of the domical contour structure. This equally applies to all embodiments disclosed herein. The ability to use the fasteners 33 in this manner will enhance supplemental bone grafting as the grafts may be partially secured with the fasteners 33.

Figure 3:
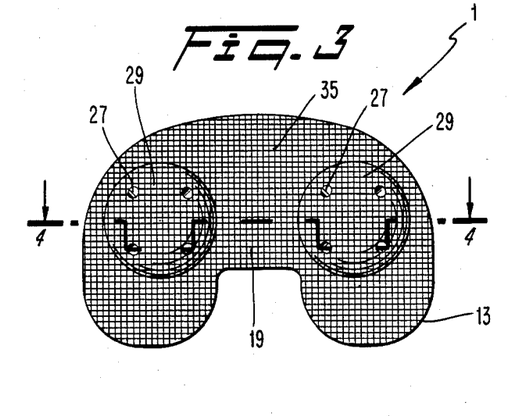
FIG. 3 shows a bottom view of the embodiment illustrated in FIGS. 1 and 2.

With reference now to FIGS. 1 and 3, it is seen that the undersurface 19 of the tray portion 13, including the domical contours 29 is completely covered with a porous bony ingrowth material designated by the reference numeral 35 which material may comprise metallic or non-metallic mesh which has been firmly fixated to the undersurface 19 in a manner well known to those skilled in the art. The purpose for the bony ingrowth material 35 is to enhance the fixation of the prosthesis 1 to the proximal tibia by virtue of bone material in the proximal tibia ingrowing into the mesh to thereby firmly fixate the tray portion 13 and thereby the entire prosthesis 1 thereto. The use of the material 35 eliminates the requirement for fixation through the use of cement. If, however, the surgeon desires to use cement in fixating the prosthesis 1 to the proximal tibia, the entire undersurface 19 of the tray portion 13 could be made smooth, even in the region of the domical contours 29. However, in the preferred embodiment of the present invention, the undersurface 19 is completely covered with the porous bony ingrowth material 35 since, as stated above, the use of the domical contours 29 sufficiently increases the surface area of contact between the tray portion 13 and the proximal tibia so as to eliminate the necessity of fixation through cementing techniques.

In the preferred embodiment, the tray 13 may be made of a high-strength bio-compatible material such as titanium. However, if desired, other high-strength metals such as chromium-cobalt-molybdenum may be utilized. Additionally, non-metallic bio-compatible materials may be used.

Figure 4:
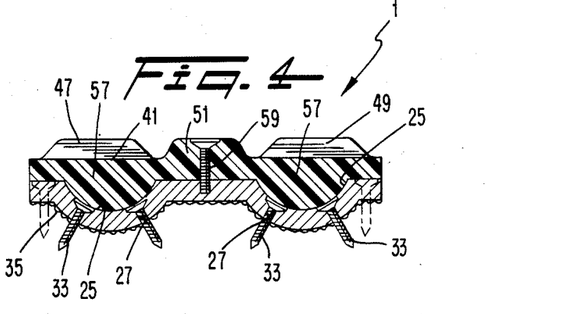
FIG. 4 shows a cross-sectional view along the line 4—4 of FIG. 3.

With reference, now, to FIGS. 1, 2 and 4, it is seen that the articular insert portion 15 includes an upper surface 41, an undersurface 43, and a periphery 45. As best seen in FIG. 2, the upper surface 41 includes a pair of generally concave indentations designated by the reference numerals 47 and 49 and which are designed to bearingly receive cooperating condyle portions of the femoral prosthesis in a manner well-known to those skilled in the art. The indentations 47 and 49 are separated from one another by a rib-like structure 51 which is designed to be received between the femoral condyles in a manner well known to those skilled in the art.

The periphery 45 of the articular insert portion 15 is designed to smoothly match the periphery 21 of the tray portion 13 so that when the tray portion 13 and the articular insert portion 15 are assembled together, the edges therebetween are smoothly engaging so as to avoid damage to surrounding tissues.

With further reference to FIGS. 1 and 4, the undersurface 43 of the articular insert portion 15 includes a flat surface 55 and a pair of domical contours designated by the reference numeral 57. The contours 57 are designed to snugly fit into the recesses 25 in the top surface 17 of the tray portion 13 so as to snugly assemble the components together. In the same manner, the flat surfaces 55 of the articular insert portion 15 are designed to lie against the flat surfaces 23 on the top surface 17 of the tray portion 13. It is important to note, with partiuclar reference to FIG. 4, that the articular insert portion 15 between said domical contours 57 and said indentations 47, 49 is of substantially uniform thickness. This design causes the portion 15 to substantially uniformly distribute forces and stresses placed thereon by normal joint movements.

With reference to FIGS. 1-4, since the facing surfaces of the tray portion 13, and the articular insert portion 15 include respective recesses 25 and contours 57, these components may not be assembled to one another by sliding contact therebetween. Thus, in order to assemble these components together, they must be assembled together in a stacking fashion which precludes the use of a dovetail type assembly means. Thus, in the embodiment of FIGS. 1-4, the components may be assembled together through a snap-fit connection or, as shown in FIG. 4, through the use of screw-type fastening means 59.

Figures 5, 6:
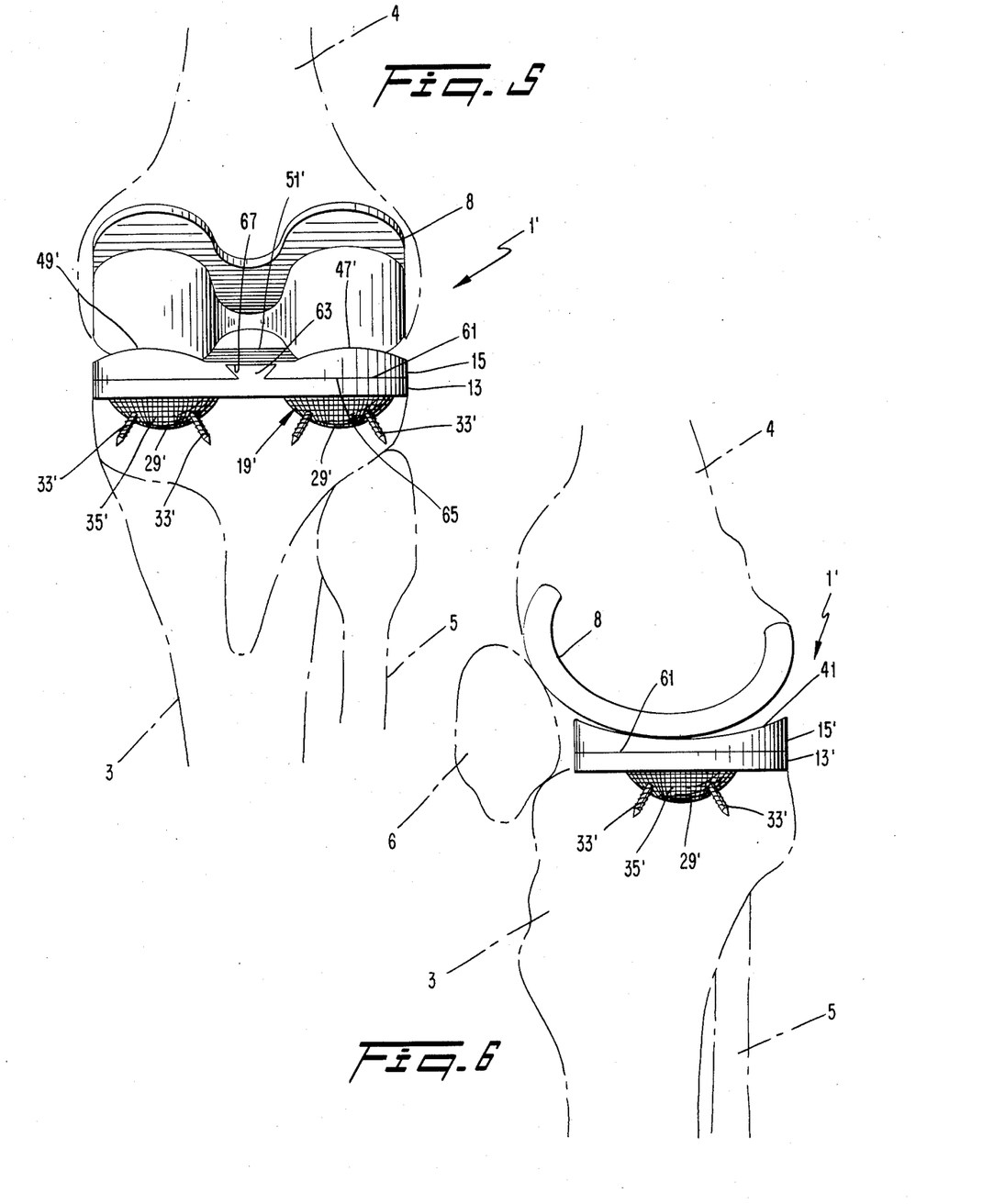
FIG. 5 shows an elevational view of a knee joint in its anterior aspect incorporating a further embodiment of the present invention.
FIG. 6 shows a side view of the embodiment of FIG. 5.
Figure 7:
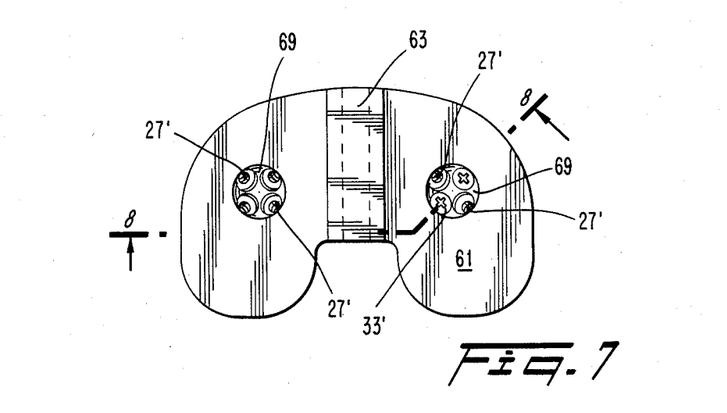
FIG. 7 shows a top view of the tray portion of the embodiment of FIGS. 5-6.
Figure 8:
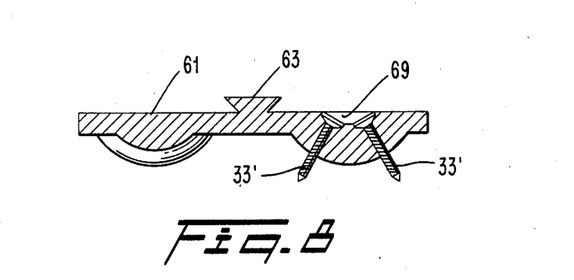
FIG. 8 shows a cross-sectional view along the line 8—8 of FIG. 7.

Reference is now made to FIGS. 5-8 wherein a further embodiment of the present invention is shown. For ease of understanding, with respect to the embodiment of FIGS. 1-4, like elements will be designated by like primed reference numerals. With reference, first to FIGS. 5 and 6, the inventive prosthesis 1' is seen in its environemnt of the tibia 3, fibula 5 and femur 4 as well as the patella 6. A distal femoral prosthesis 8 is also shown but does not form a part of the present invention. As seen with reference to FIGS. 5 and 6, the prosthesis 1' includes a tray portion 13' and an articular insert portion 15'. The tray portion 13' includes a plurality of domical contours 29' through which, preferably but not necessarily, fastening devices 33' may extend. As before, the entire undersurface 9' of the tray portion 13' is covered with porous bony ingrowth material 35' which, as before, enhances the fixation of the prosthesis to the proximal tibia.

The tray portion 15' includes a top surface 41' including the concavities 47' and 49' and the rib-like portion 51'.

All of the structure described above regarding the embodiment of FIGS. 5-8 is substantially identical to the corresponding structure in the embodiment of figures 1-4. Where the embodiment of FIGS. 5-8 differs from the embodiment of FIGS. 1-4, is in the interface between the tray portion 13' and the articular insert portion 15'. As seen in FIGS. 5-8, the upper surface 61 of the tray portion 13' is completely flat except for the presence of a dovetail-type protrusion 63 centrally located thereon. In a corresponding way, the lower surface 65 of the articular insert portion 15' is completely flat except for a dovetail-type recess 67 formed therein and designed to slidably receive, in assembly, the dovetail protrusion 63 of the tray portion 13'. Thus, with the interface between the tray portion 13' and the articular insert portion 15' being flat, the two components may be assembled together by sliding the articular insert portion recess 67 over the tray portion 13' dovetail protrusion 63 so as to snugly assemble the components together.

With reference to FIGS. 5 and 6, it is seen that the fasteners 33' preferably but not necessarily extend through the domical contours 29' in directions substantially radially emanating from the respective center of curvature of the respective contours 29', as is the case in the embodiment of FIGS. 1-4. As may be seen with reference to FIGS. 7 and 8, since the surface 61 is flat and does not include recesses such as those which are designated by the reference numeral 25 in FIG. 2, it is seen that the starting points of the respective holes 27' are closely adjacent one another as opposed to the spacing of the holes best seen in FIGS. 2 and 3. Since the surface 61 must be devoid of any protruding objects so as to enable the articular insert portion to be slid thereover, in assembly, the starting point for the holes 27' may be located in a slightly recessed chamber designated by the reference numeral 69 in FIG. 8 so as to ensure that the flatness of the surface 61 will not be compromised.

The materials from which the tray portion 13' may be manufactured are the same as those which were described hereabove with reference to the tray portion 13'. With regard to the articular insert portions 15 and 15', in the preferred embodiments, these structures are made of a strong, low-friction, bio-compatible material such as plastic. A preferred plastic for use in manufacturing the portions 15 and 15' comprises polyethylene.

Figure 9:
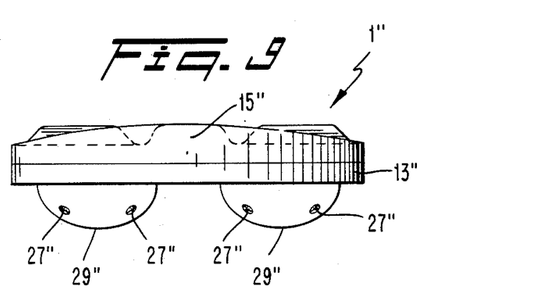
FIG. 9 shows an anterior elevation view of a further embodiment of the present invention.

With reference now to FIG. 9, a further embodiment of the present invention is designated by the reference numeral 1" and is seen to include an articular insert portion 15" which may, if desired, be made in accordance with the teachings of either of the embodiments of FIGS. 1-4 or 5-8. Further, the embodiment of FIG. 9 includes a tray portion 13" which may, if desired, interface with the articular insert portion 15" in the manner taught by either of the embodiments of FIGS. 1-4 or 5-8. The device 1" differs from the embodiments of FIGS. 1-4 and 5-8 in the specific shape of the domical contours 29" thereof. In the embodiment of FIG. 9, the domical contours 29' are formed of an elliptical configuration formed by rotating a curved line corresponding to the surface of an ellipse about its axis of rotation. Thus, it may be seen that the contours 29" of the embodiment of FIG. 9 are slightly flatter and more laterally elongated than is the case in the embodiments of FIGS. 1-4 and 5-8. As stated hereinabove, any curved domical contour surface is considered to form a part of the present invention. Thus, in theory, any domical surface which may be created through the rotation of a curved line about its axis of rotation would be considered to be included in the teachings of the present invention. Such a requirement is necessary because the recesses 9 and 11 which must be formed in the proximal tibia (FIG. 2) must be made within the purview of the present invention through the use of a reaming device including a rotary cutting head. Thus, any rotary cutting head which may have a cutting surface thereof defined by the rotation of a curved line about its axis of rotation may be utilized to form the appropriate recesses 9 and 11 into which the domical contours of the inventive tray portion 13' or 13", may be inserted.

When a surgeon is deciding which domical contour should be used in installing the prosthesis of the present invention on the proximal tibia, several factors must be taken into account. As the degree of convexity is decreased, less surface area of engagement exists and thus the fixation will have a lessened chance of success. On the other hand, the larger the degree of convexity, the greater amount of bone which must be removed from the proximal tibia so as to facilitate installation. Thus, the surgeon must strike a balance between increasing the area of fixation while limiting the amount of bone removal. In the present invention, it has been found that the optimal extent of protrusion of the domical contours is from 3 to 6 millimeters from the undersurface of the tray portion. Keeping the extent of protrusion at a particular fixed level, the surface area of the domical contour may be increased by increasing the radius of curvature of surface thereof. Thus, in each particular case, the surgeon may study the proximal tibia to determine the appropriate radius of curvature which should be employed in the domical contours for optimum fixation and installation.

If desired, depending upon the particular characteristics of the proximal tibia, the surgeon may elect to utilize a prosthesis having domical contours of differing heights and/or radii of curvature. Thus, a particular prosthesis may include two domical contours, for example, having different extents of protrusion but with differing radii of curvature so that each domical contour displaces the same volume of bone tissue. On the other hand, the surgeon may choose to utilize a tray portion having domical contours of equal height but of differing radii of curvature so that the domical contours displace differing volumes of bone tissue. Such options are always available to the surgeon depending upon the particular configuration and shape of each proximal tibia. Additionally, truncated domical contours may be utilized where indicated.

Figure 10:
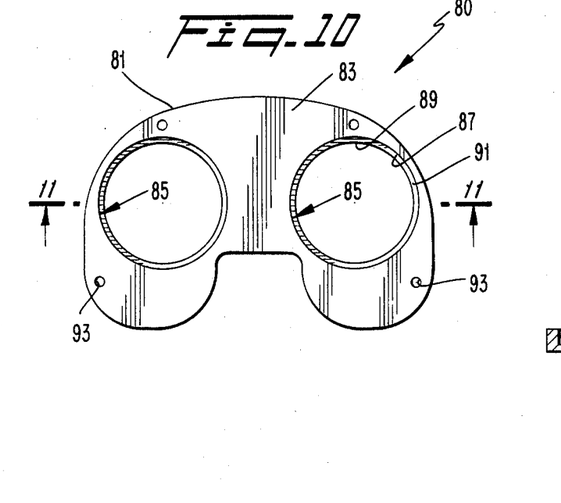
FIG. 10 shows a top view of a template used in preparing the posterior tibia for the attachment thereto of the inventive prosthesis.
Figure 11:
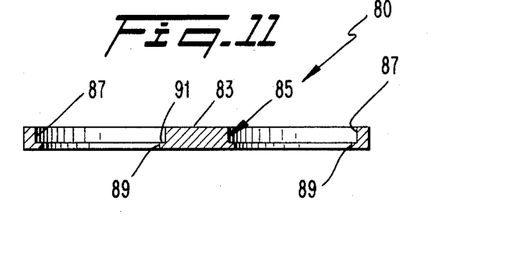
FIG. 11 shows a cross-sectional view along the line 11—11 of FIG. 10.

Reference is now made to FIGS. 10 and 11 wherein a template 80 is depicted which may be utilized by the surgeon to locate the areas on the proximal tibia where bone tissue is to be removed so as to create domical recesses which are to receive the domical contours of the undersurface of the tray portion of the improved prosthesis. As shown in FIG. 10, the template 80 includes a periphery 81 designed to substantially match the periphery of the proximal tibia as best seen in FIG. 2. Within the top surface 83 of the template, a plurality of openings 85 are formed therethrough. As best seen with reference to FIG. 11, the openings 85 are characterized by including a portion 87 of enlarged diameter, a portion 89 of reduced diameter and a shoulder 91 therebetween and connecting the portions 87 and 89. The shoulder is provided for a purpose to be described hereinafter. With reference to FIG. 10, the template 80 also includes a plurality of small holes 93 formed therethrough. The holes 93 are provided so as to enable the surgeon to utilize a plurality of pins (not shown) to fixate the template 80 in a secure position on the upper surface of the resected proximal tibia so as to facilitate the reaming operation without fear that the template 80 will move during the process. The shoulders 91 are provided so as to interact with peripheral surfaces formed on the reaming head so as to limit the extent of penetration of the reaming head into the tibial surface as will be described in greater detail hereinafter.

Figure 12:
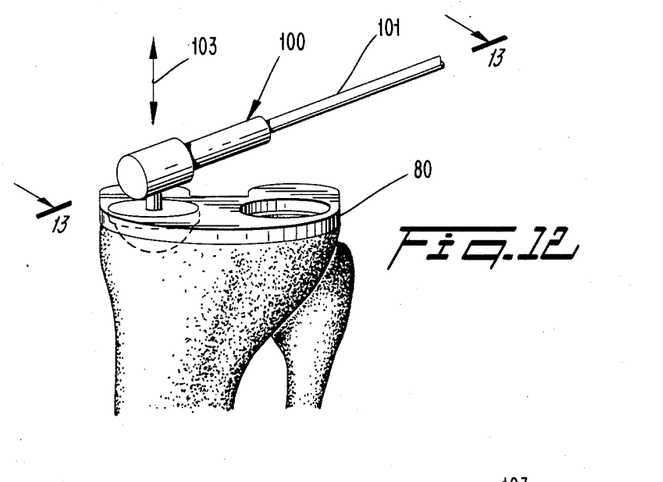
FIG. 12 shows a side perspective view of the proximal tibia having the template of FIGS. 10 and 11 placed thereon and showing a reaming device being utilized in accordance with the teachings of the present invention.
Figure 13:
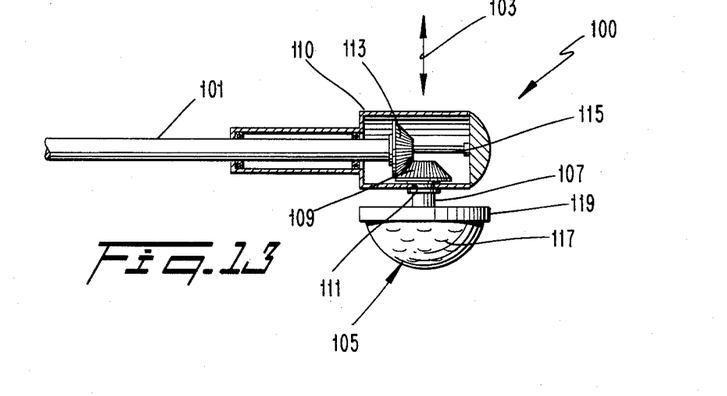
FIG. 13 shows a cross-sectional view along the line 13—13 of FIG. 12.

Reference is now made to FIGS. 12 and 13 wherein a reaming device generally designated by the reference numeral 100 and designed to be utilized in installing the inventive prosthesis is shown. With reference first to FIG. 12, the template 80 is seen installed over the proximal tibia and a reaming device 100 is seen entering one of the holes 85 in the template 80 to ream a concave surface in the proximal tibia. As seen in FIG. 12, the drive shaft 101 of the reaming device 100 is at an angle to the axis 103 of rotation of the reamer head generally designated by the reference numeral 105 in FIG. 13.

As seen in FIG. 13, the reamer head 105 includes a drive shaft 107 having a pinion gear 109 attached to its proximal end. A housing 110 is provided having an opening 111 therethrough through which the shaft 107 extends and the opening 111 also comprises a bearing for supporting the shaft 107 for rotation perpendicular to the direction of elongation of the opening 111. Within the housing 110 is a further pinion gear 113 which is connected at the distal end of the drive shaft 101 and which has depending therefrom a guide shaft 115 having a distal end inserted into an opening (not shown) in a wall of the housing 110 so as to enable the gear 113 to be rotated in a controlled manner.

With further reference to FIG. 13, it is seen that the reamer head 105 includes a plurality of cutting protrusions 117 thereon which facilitate the removal of bone tissue from the proximal tibia. As further seen in FIG. 13, at the proximal end of the reamer head 105, an annular protrusion 119 is formed. The protrusion 119 has a circular periphery and is designed to be of slightly smaller diameter than the diameter of the opening 87 of the template so that the surface 119 may enter the template opening 87, but the surface 119 is slightly larger in diameter than the inner diameter of the shoulder 91 so that interengagement of the protrusion 119 and the shoulder 91 limits the axial extent to which the reamer device 105 may be inserted into the proximal tibia tissue. The largest diameter of the cutting surface of the reamer device 105 is just below the protruding surface 119 and this cutting surface is designed to be slightly smaller in diameter than the diameter of the opening 89 of the template 80 so that the cutting surface may be extended completely through the opening 89 to facilitate cutting of the bone tissue of the proximal tibia.

As stated above, in the preferred embodiment of the present invention, it is preferred that the angle between the axis of rotation 103 of the reamer device 105 and the axis of rotation of the drive shaft 101 be between 45° and 90°. This angle range is chosen because with the reamer head 105 so angled with respect to the drive shaft 101, the surgeon may most easily insert the device 100 into an incision and utilize it in removing the appropriate bone tissue. It is stressed in this regard that the particular angle chosen is chosen depending upon the particular circumstances of the particular surgery and in some cases with the knee flexed so that the femur and tibia lie at substantially right angles to one another, the drive shaft 101 may be disposed in axial alignment with the axis 103 of rotation of the reamer 105. If desired, instead of the gears 109 and 113, a flexible coupling may be utilized which enables the angle of rotation between the reamer 105 and the drive shaft 101 to be infinitely varied.

With the prosthesis 1, template 80 and reamer device 100 having been described, the method of installation of the inventive prosthesis 1 will not be described.

Firstly, the proximal tibia is resected in a manner well known to those skilled in the art so as to provide a flat proximal surface of proper orientation to the tibial shaft. Thence, the template 80 is placed over this flat proximal tibial surface and is secured thereto through the use of pins (not shown). Thereafter, the reamer device 100 is inserted into the incision and the cutting head thereof is inserted sequentially through the respective holes 85 in the template 80 so as to facilitate the removal of bone tissue from the proximal tibia. Interaction of the annular protrusion 119 of the reamer head 105 with one of the shoulders 91 of the respective openings 85 in the template 80 will indicate to the surgeon that the maximum extent of penetration of the reamer head 105 has been accomplished Thereafter, the reamer head is inserted into all subsequent openings 85 sequentially so as to complete the creation of the domical recesses in the proximal tibia.

Thereafter, the tray portion 13, 13', 13'', of the prosthesis 1 is placed over the resected and reamed proximal tibial surface and attached thereto, preferably through the use of the screws 27, 27', 27''. Thereafter, the articular insert portion in installed over the tray portion through whatever means is included in the particular embodiment used, whether screw-type fasteners, dovetail-type fasteners or the like. Then, the surgery is completed through those techniques known to those skilled in the art including the closing of the appropriate incision or incisions.

Thus, an invention has been described in terms of the improved prosthesis and in terms of the improved template and reamer device which are utilized in its installation. Various changes, modifications, alterations and the like may be contemplated by those skilled in the art without departing from the intended spirit and scope of the present invention. Accordingly, it is intended that the present invention only be limited by the terms of the appended claims.

We claim:

1. An improved tibial prosthesis for attachment to the subchondral plates of a tibia, the plates having a lateral plateau and a medial plateau, said prosthesis comprising:
   (a) an elongated tray member having an upper surface and an undersurface, said undersurface having a contour consisting of a flat surface having a plurality of domical protrusions extending outwardly therefrom, said plurality of protrusions being arranged with respect to said undersurface such that, in use, said medial plateau and said lateral plateau each have at least one protrusion attached thereto, said undersurface being adapted to be surgically attached to a corresponding contour surgically prepared on a proximal tibial plateau such that forces applied on said prosthesis are spread throughout said tibia substantially uniformly, and
   (b) an articular insert portion having an upper surface and an undersurface, said insert portion upper surface including an articular surface adapted to bearinly receive cooperating condyles of a distal femur, said insert portion undersurface being matingly engaged to said tray portion upper surface 2. The invention of claim 1, wherein each of said domical protrusions has an outer surface comprising a part spherical surface.

3. The invention of claim 2, wherein said part spherical surface is less than a hemisphere.

4. The invention of claim 1, wherein each of said domical protrusions has an outer surface comprising a part elliptical surface.

5. The invention of claim 1, wherein said tray portion upper surface includes one of a dovetail recess or a dovetail protrusion and said articular insert portion undersurface includes the other of said dovetail recess or dovetail protrusion, said tray portion being attached to said articular insert portion by interengagement of said dovetail protrusion with said dovetail recess.

6. The invention of claim 1, wherein said cooperating condyles form a portion of a distal femoral prosthesis surgically mounted on said distal femur.

7. The invention of claim 1, wherein said tray portion undersurface is covered with a porous bony ingrowth material.

8. The invention of claim 11, wherein said porous material comprises a mesh.

9. The invention of claim 1, wherein said tray portion is made of metal and said articular insert portion is made of plastic.

10. An improved tibial prosthesis for attachment to subchondral plates of a tibia, the plates having a lateral plateau and a medial plateau, said prosthesis comprising:
    (a) an elongated undersurface having a domical contour which is adapted to be surgically prepared on a proximal tibial plateau;
    (b) an upper articular surface adapted to bearingly receive cooperating condyles of a distal femur;
    wherein said domical contour consists of a flat surface having a plurality of domes extending outwardly from said flat surface, each of said medial plateau and said lateral plateau, in use, having at least one dome attached thereto such that forces applied on said prosthesis are spread throughout said tibia substantially uniformly.

* * * * *

UNITED STATES PATENT AND TRADEMARK OFFICE
CERTIFICATE OF CORRECTION

PATENT NO. : 4,808,185
DATED : February 28, 1989
INVENTOR(S) : BRAD L. PENENBERG It is certified that error appears in the above-identified patent and that said Letters Patent is hereby corrected as shown below:

Claim 1, lines 19 and 20 of the claim, "bea-rinly" should read --bea-ringly--.

Claim 8, line 1 of the claim, "11" should read --7--.

Signed and Sealed this

Twenty-ninth Day of August, 1989

Attest:

DONALD J. QUIGG

Attesting Officer

Commissioner of Patents and Trademarks